(12) United States Patent
Johnson et al.

(10) Patent No.: US 6,938,457 B2
(45) Date of Patent: Sep. 6, 2005

(54) PHASED ARRAY ULTRASONIC REFERENCE BLOCK

(75) Inventors: Paul Johnson, Iron Station, NC (US); Matthew McGrath, Anthem, AZ (US); David Galbally, San Jose, CA (US)

(73) Assignee: General Electric Company, Schenectady, NY (US)

( * ) Notice: Subject to any disclaimer, the term of this patent is extended or adjusted under 35 U.S.C. 154(b) by 148 days.

(21) Appl. No.: 10/680,185

(22) Filed: Oct. 8, 2003

(65) Prior Publication Data

US 2005/0076703 A1 Apr. 14, 2005

(51) Int. Cl.[7] .......................... G01D 18/00; G01B 3/56
(52) U.S. Cl. ........................................ 73/1.86; 33/534
(58) Field of Search ................... 73/1.86, 1.03, 73/1.82; 33/534

(56) References Cited

U.S. PATENT DOCUMENTS

| | | | | |
|---|---|---|---|---|
| 5,036,707 A | * | 8/1991 | Paciej et al. ................... | 73/637 |
| 5,665,893 A | * | 9/1997 | Smith .......................... | 73/1.82 |
| 5,837,880 A | * | 11/1998 | Shakinovsky et al. ........ | 73/1.86 |
| 6,415,644 B1 | * | 7/2002 | Rockwood et al. .......... | 73/1.86 |
| 6,532,675 B2 | * | 3/2003 | Letourneau ................... | 33/277 |
| 6,671,972 B2 | * | 1/2004 | Mitterreiter et al. .......... | 33/534 |

* cited by examiner

Primary Examiner—Hezron Williams
Assistant Examiner—Jacques M. Saint-Surin
(74) Attorney, Agent, or Firm—Harness Dickey & Pierce, P.L.C.

(57) ABSTRACT

The calibration device includes a guide surface and an angle gauge supported relative to the guide surface on a first side of the guide surface. The angle gauge is adjustable to measure a skew angle of the ultrasonic transducer on the guide surface. The angle gauge is slidable along a length of the guide surface. The angle gauge is rotatably supported parallel to the guide surface. A gauge block rotatably supports the angle gauge.

24 Claims, 7 Drawing Sheets

PHASED ARRAY ULTRASONIC REFERENCE BLOCK

FIELD OF THE INVENTION

The present invention relates to calibration reference blocks, and more particularly a reference block for calibrating a skew angle of an ultrasonic transducer.

BACKGROUND OF THE INVENTION

An ultrasonic transducer emits an ultrasonic sound beam incident to a material. The ultrasonic beam is reflected back as an echo from a reflector. The echo response can indicate characteristics of the path traveled. The ultrasonic beam can be steered to a desired point in space by programming an induced angle and a skew angle. The ultrasonic transducer emits the ultrasonic beam corresponding to the programmed induced and skew angles.

The ultrasonic transducer is used to evaluate and inspect non-observable, internal conditions of structures. In some instances, the ultrasonic transducer is used to evaluate wall thickness of piping, weld integrity, stress corrosion and/or cracking. The nuclear energy industry, in particular, implements ultrasonic transducers to evaluate various components of a nuclear reactor. Other industries, such as the petroleum and aerospace industries, implement ultrasonic transducers to inspect components for metal cracking, weld integrity and metal thickness.

Prior to inspecting a component, the ultrasonic transducer must be calibrated. Calibration is used to program appropriate beam angles and to focus the beam at the desired point in space. Traditional reference blocks enable accurate calibration of induced angles only.

SUMMARY OF THE INVENTION

Accordingly, the present invention provides a calibration device to calibrate an ultrasonic transducer. The calibration device includes a guide surface and an angle gauge supported relative to the guide surface on a first side of the guide surface. The angle gauge is adjustable to measure a skew angle of the ultrasonic transducer on the guide surface.

In one feature, the angle gauge is slidable along a length of the guide surface.

In another feature, the angle gauge is rotatably supported parallel to the guide surface. A gauge block rotatably supports the angle gauge.

In yet another feature, a first calibration surface is formed in the first side of the guide surface. The ultrasonic transducer rests on the guide surface to transmit ultrasonic waves to the first calibration surface.

In still another feature, a second calibration surface is formed in the first side of the guide surface. The ultrasonic transducer rests on the guide surface to transmit ultrasonic waves to the second calibration surface.

In another feature, the angle gauge is movable to be supported parallel to the guide surface on a second side of the guide surface. A calibration surface is formed in the second side of the guide surface. The ultrasonic transducer rests on the guide surface to transmit ultrasonic waves to the calibration surface.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Referring now to FIGS. 1 through 4, a calibration device 10 is shown. The calibration device 10 includes a calibration block 12 and an angle gauge 14 slidably attached thereto. The calibration block 12 includes a top guide surface 16, a bottom guide surface 18, a front face 20 and a back face 22. In accordance with one configuration, the angle gauge 14 is mounted to a groove 21 and is slidable across the front face 20 (see FIG. 1). In accordance with another configuration, the angle gauge 14 is mounted to a groove 23 and slidable across the back face 22 (see FIG. 2).

The calibration block 12 further includes a plurality of calibration or reflector surfaces. The reflector surfaces are arcuate in form, each having a defined radius. Although the reflector surfaces are arcuate, it is appreciated that the reference surfaces can each be formed in other shapes based on the geometry of a component to be inspected.

A first reflector surface 24 is defined by a first radius ($r_1$) and a second reflector surface 26 is define by a second radius ($r_2$). A front edge 28 of the top guide surface 16, a front edge 30 of the bottom guide surface 18 and edges 32,34 of the first and second reflector surfaces 24,26, respectively, define boundaries of the front face 20. A third reflector surface 36 is defined by a third radius ($r_3$) and a fourth reflector surface 38 is defined by a fourth radius. A fifth reflector surface 40 is defined by a fifth radius ($r_5$). A back edge 42 of the top guide surface 16, a back edge 44 of the bottom guide surface 18 and edges 46,48,50, of the third, fourth and fifth reflector surfaces 36,38,40, respectively, define boundaries of the back face 22.

Figure 1:
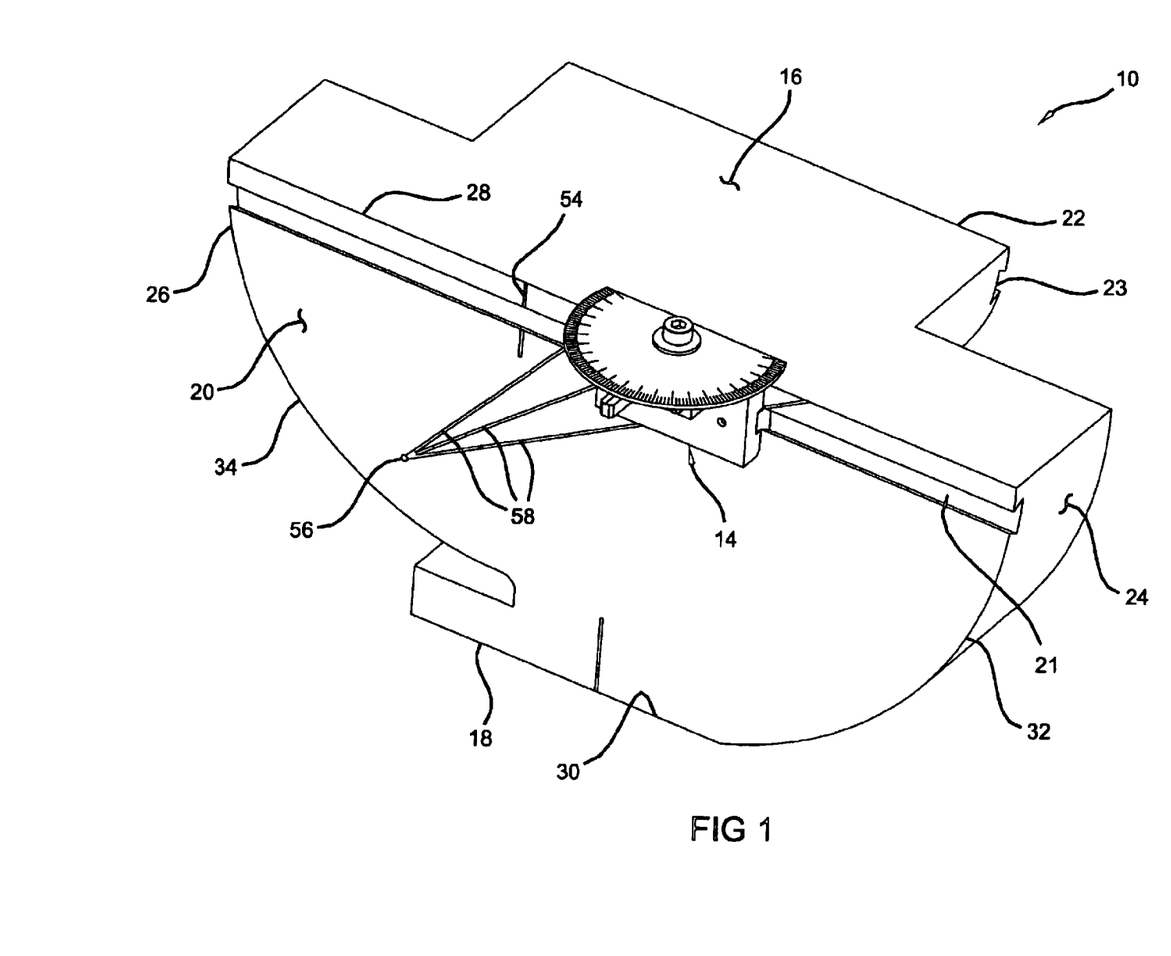
FIG. 1 is a front perspective view of a calibration device.
Figure 3:
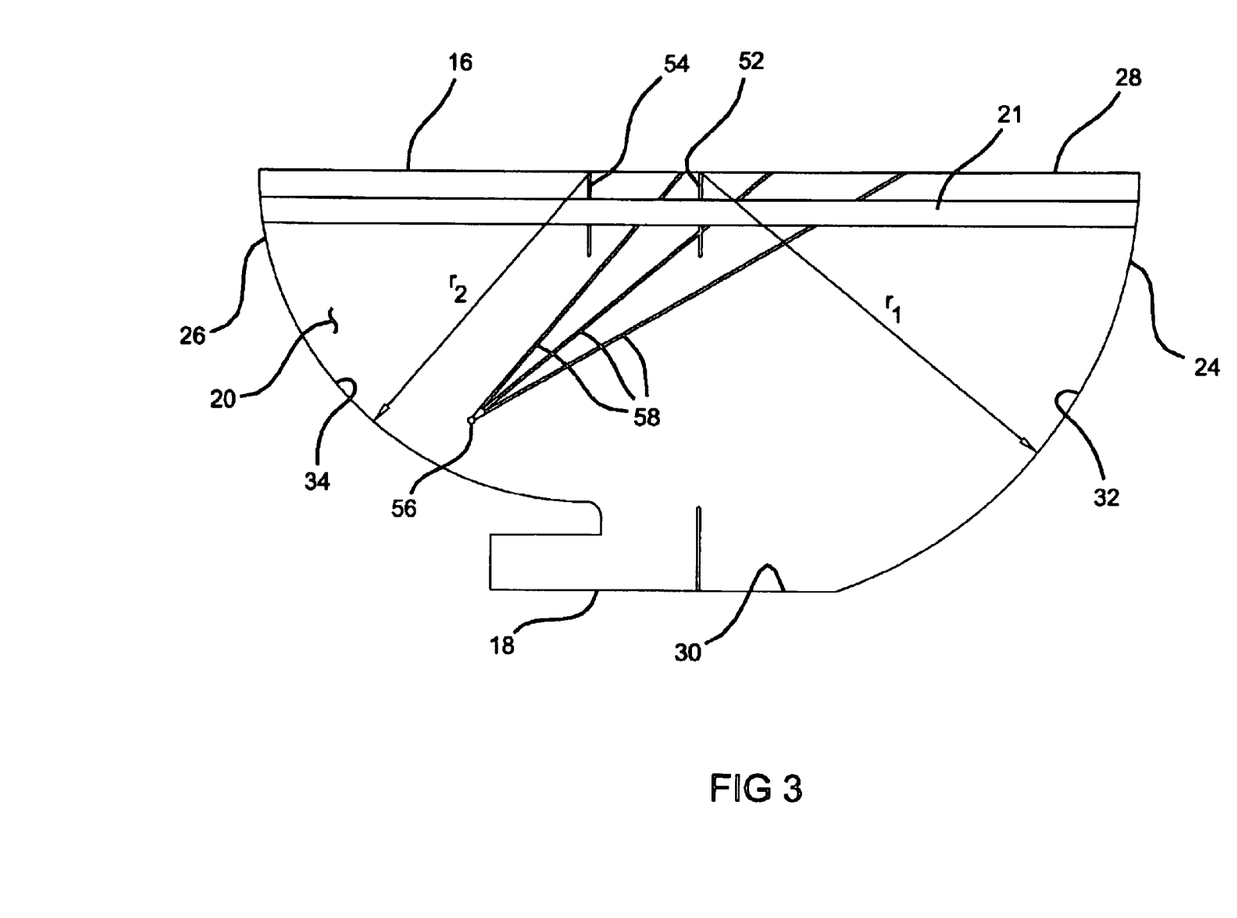
FIG. 3 is a front elevation of the calibration device.

With reference to the front face 20, a first scribed line 52 indicates the center point of the first radius. A second scribed line 54 indicates the center point of the second radius. A first index hole 56 is bored in the front face 20 adjacent the second reflector surface 26. A series of scribed angle lines 58 extend at varying angles from the first index hole 56 to the front edge 28. A first angle line extends at 40°, a second angle line extends at 50° and a third angle line extends at 60°, each relative to vertical. It is appreciated, however, that the particular angles of the scribed angle lines 58 can vary as design requirements dictate.

Figure 2:
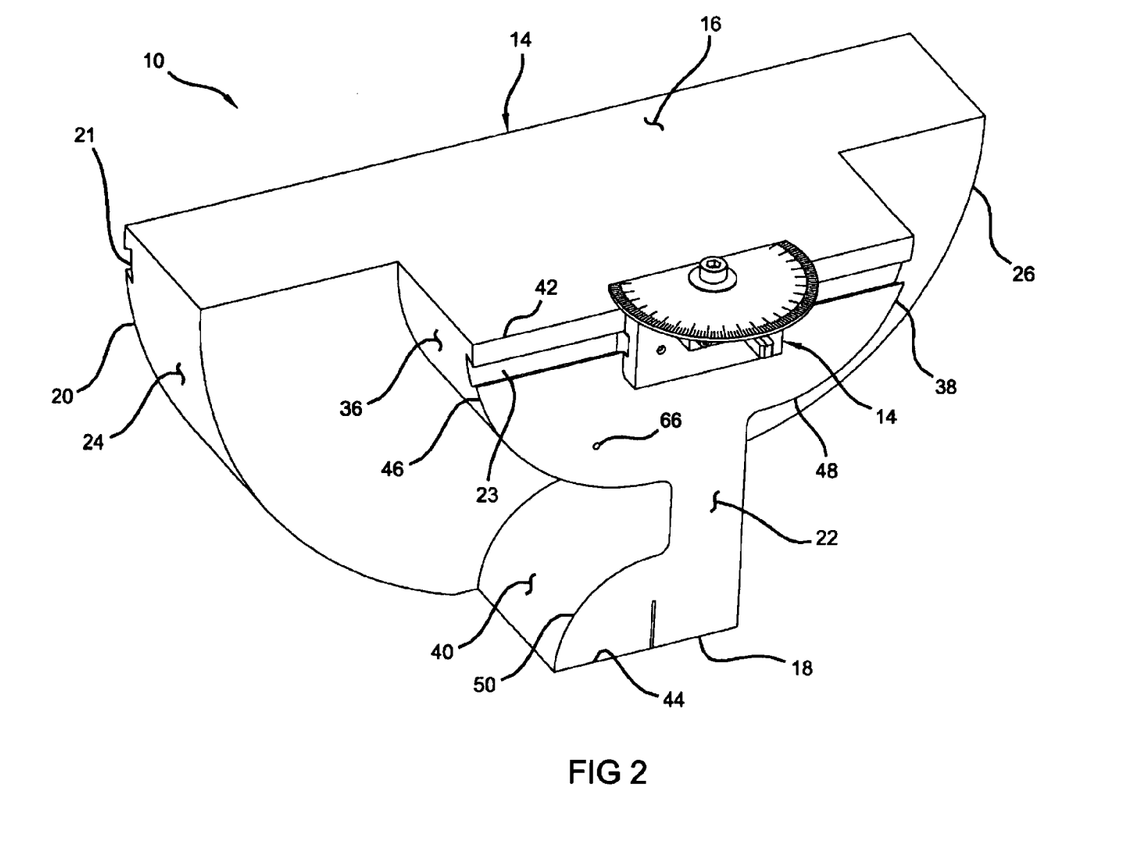
FIG. 2 is a rear perspective view of the calibration device.
Figure 4:
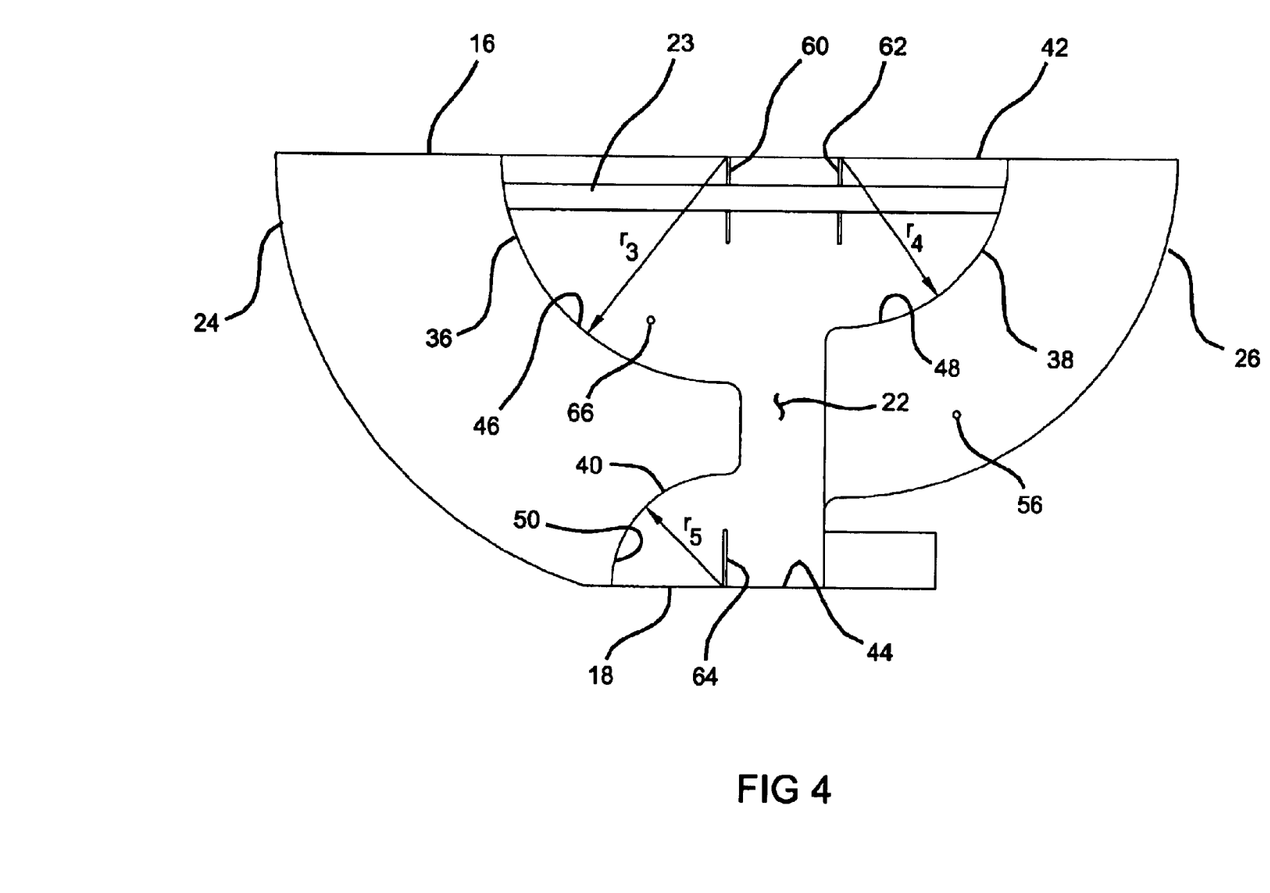
FIG. 4 is a rear elevation of the calibration device.

With reference to the back face 22, a third scribed line 60 indicates the center point of the third radius and a fourth scribed line 62 indicates the center point of the fourth radius. A fifth scribed line 64 indicates the center point of the fifth radius. A second index hole 66 is bored into the back face 22 adjacent the third reflector surface 36.

Figure 5:
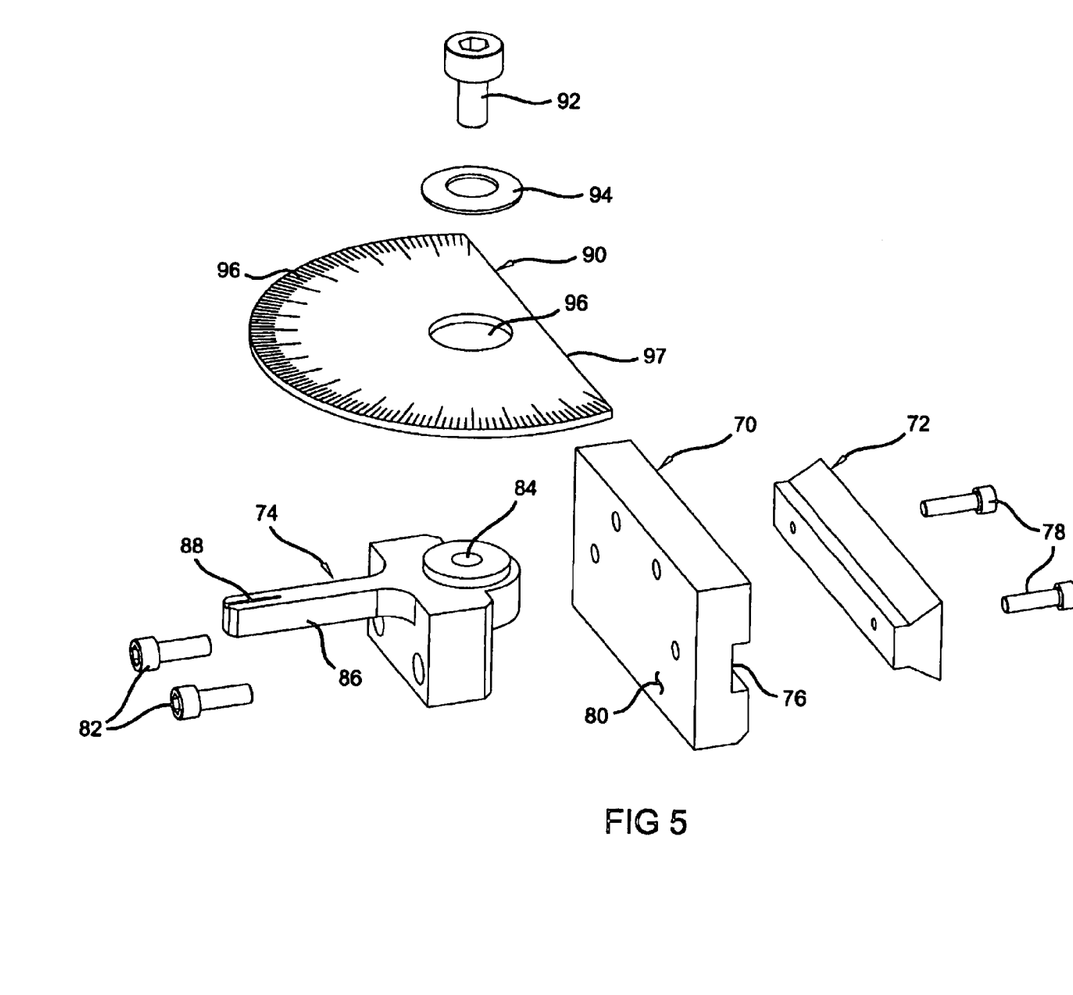
FIG. 5 is an exploded view of an angle gauge of the calibration device.

Referring now to FIG. 5, the angle gauge 14 includes a slide plate 70 to which a dovetail rail 72 and a support 74 are attached. The dovetail rail 72 seats within a groove 76 of the slide plate 70 and is fixed therein by fasteners 78. The support 74 is fixed adjacent to a face 80 of the slide plate 70 by fasteners 82. The support 74 includes a bore 84 and an indicator arm 86 having a scribed line 88. An angle plate 90 is rotatably supported on the support 74. A flared side of the dovetail rail 72 seats within either of the grooves 21,23 to enable sliding of the angle gauge 14 across the front and back faces 20,22, respectively.

A fastener 92 is received through a belleville or spring washer 94 and a hole 96 formed through the angle plate 90. The fastener 92 is threaded into the bore 84 to secure the angle plate 90 to the support 74. The spring washer 94 applies sufficient force against the angle plate 90 to prevent undesired rotation of the angle plate 90 about the fastener 92. When rotation of the angle plate 90 is desired, an operator applies upward force against that of the spring washer 94 and rotates the angle plate 90 about the fastener 92. The particular angle to which the angle plate 90 is rotated is determined by alignment of the line 88 with angle markers 96 scribed into the angle plate 90. The angle plate further includes an alignment edge 97 that is aligned parallel to an object for which the angle of is to be determined.

Figure 6:
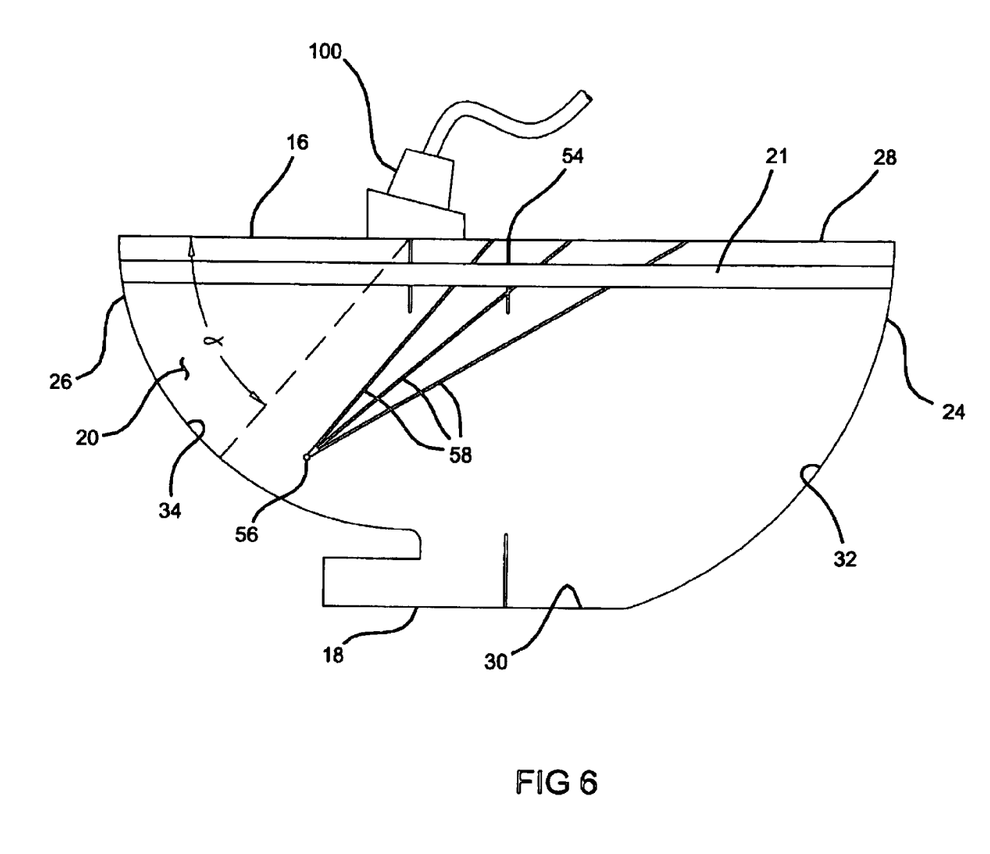
FIG. 6 is the front elevation of FIG. 3 illustrating the calibration device with the angle gauge removed and an ultrasonic transducer placed on the calibration device.
Figure 7:
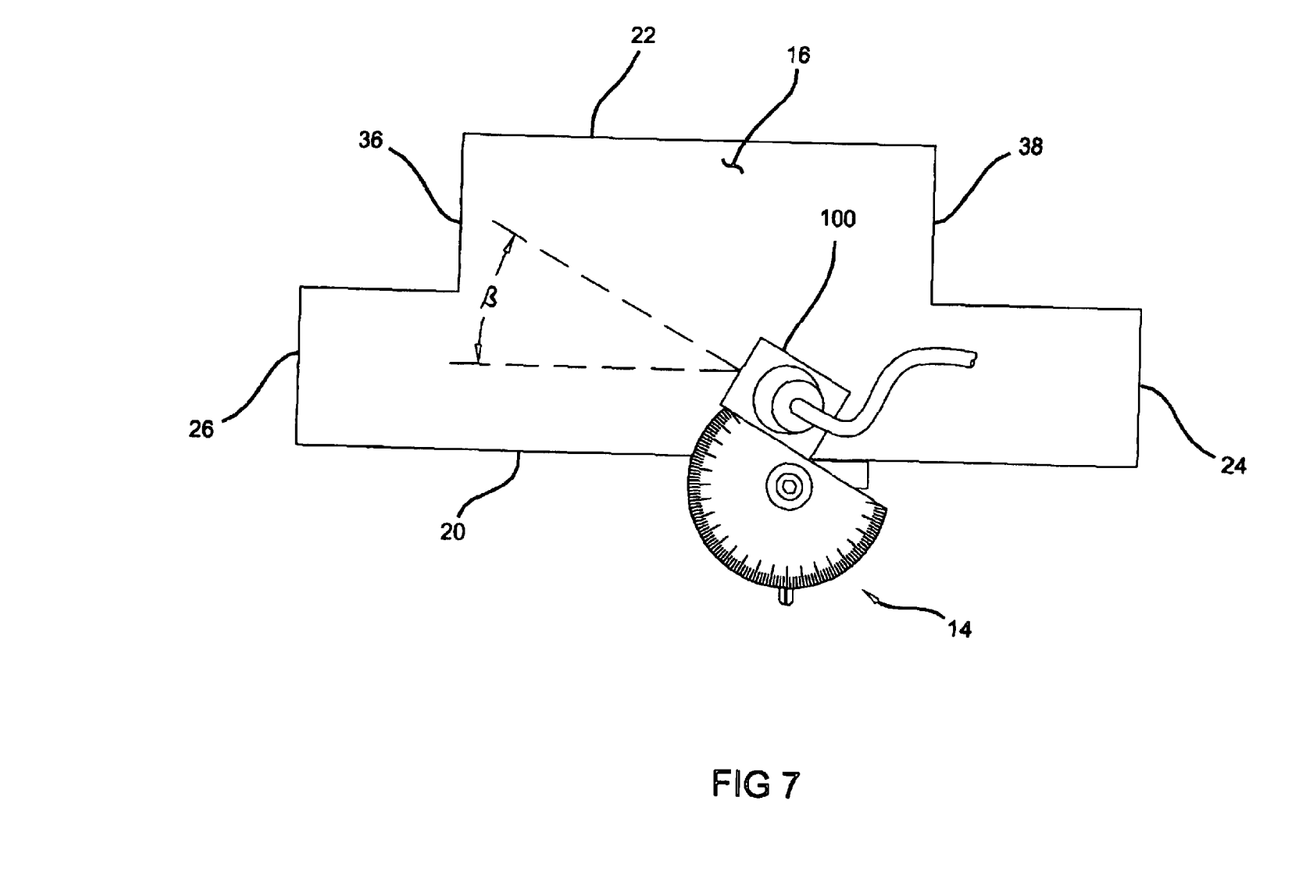
FIG. 7 is a plan view of the calibration device illustrating alignment of the angle gauge with the ultrasonic transducer.

Referring now to FIGS. 6 and 7, use of the calibration device 10 will be described. An ultrasonic transducer 100 is initially programmed with a desired induced angle (α) and a desired skew angle (β) to focus the beam at a point in space. The ultrasonic transducer 100 is set on one of the top or bottom guide surfaces 16,18 depending on the particular reflector surface required. The reflector surface is selected based on the geometry of the component. For example, if the component is a pipe with a 2 inch outside diameter, a reflector surface having a 4 inch radius is selected.

In the exemplary embodiment of FIGS. 6 and 7, the ultrasonic transducer 100 is set on the top guide surface 16. The beam of the ultrasonic transducer 100 is directed toward the second reflector surface 26. The ultrasonic transducer 100 is slid across and rotated in place on the top guide surface 16 until a desired amplitude response is achieved. The desired amplitude response may be a maximum amplitude response. However, it is appreciated that an amplitude response that is less than the maximum amplitude response may be sufficient for the particular material analysis. In such a case, the desired amplitude response is defined as a sufficient amplitude response. As an example, for an induced angle of 45°, the desired amplitude response is achieved when the ultrasonic transducer 100 is at a 45° angle to the second reflector service 26. For 45°, the ultrasonic transducer 100 would be approximately aligned with the center point of the radius or the second scribed line 54.

Once the desired amplitude response is achieved, the induced angle (α) and the skew angle (β) are confirmed. The induced angle is confirmed using the first index hole 56. The index holes are perfect reflectors. As a result, the desired amplitude response is easily discerned with the beam directed at the first index hole 56. The induced angle is confirmed by comparing the position of the ultrasonic transducer 100 with respect to the angle lines 58. The skew angle is confirmed by aligning the angle gauge 14 with the ultrasonic transducer 100. The angle plate 90 is rotated until the alignment edge 97 is adjacent and parallel to the ultrasonic transducer 100. The skew angle is determined by observing the particular angle marker 96 to which the line 88 indicates.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A calibration block to calibrate an ultrasonic transducer, comprising:

a guide surface; and an angle gauge supported relative to said guide surface on a first side of said guide surface, said angle gauge adjustable to measure a skew angle of said ultrasonic transducer on said guide surface.

2. The calibration block of claim 1, wherein said angle gauge is slidable along a length of said guide surface.

3. The calibration block of claim 1, wherein said angle gauge is rotatably supported parallel to said guide surface.

4. The calibration block of claim 3, further comprising:

a gauge block rotatably supporting said angle gauge.

5. The calibration block of claim 1, further comprising:

a first calibration surface formed in said first side of said guide surface; and wherein said ultrasonic transducer rests on said guide surface to transmit ultrasonic waves to said first calibration surface.

6. The calibration block of claim 1, further comprising:

a second calibration surface formed in said first side of said guide surface; and wherein said ultrasonic transducer rests on said guide surface to transmit ultrasonic waves to said second calibration surface.

7. The calibration block of claim 1, wherein said angle gauge is movable to be supported parallel to said guide surface on a second side of said guide surface.

8. The calibration block of claim 7, further comprising:

a calibration surface formed in said second side of said guide surface; and wherein said ultrasonic transducer rests on said guide surface to transmit ultrasonic waves to said calibration surface.

9. A calibration block to calibrate an ultrasonic transducer, comprising:

a guide surface;

first and second calibration surfaces adjacent to a first side of said guide surface; and an angle gauge supported relative to said guide surface on a first side of said guide surface, said angle gauge adjustable to measure a skew angle of said ultrasonic transducer on said guide surface.

10. The calibration block of claim 9, wherein said first calibration surface is arcuate and defines a first radius.

11. The calibration block of claim 9, wherein said second calibration surface is arcuate and defines a second radius.

12. The calibration block of claim 9, wherein said angle gauge is slidable along a length of said guide surface.

13. The calibration block of claim 9, wherein said angle gauge is rotatably supported parallel to said guide surface.

14. The calibration block of claim 13, further comprising:

a gauge block rotatably supporting said angle gauge.

15. The calibration block of claim 9, wherein said ultrasonic transducer rests on said guide surface to transmit ultrasonic waves to said first calibration surface.

16. The calibration block of claim 9, wherein said ultrasonic transducer rests on said guide surface to transmit ultrasonic waves to said second calibration surface.

17. The calibration block of claim 9, wherein said angle gauge is movable to be supported parallel to said guide surface on a second side of said guide surface.

18. The calibration block of claim 17, further comprising:
a third calibration surface adjacent to said second side of said guide surface; and
wherein said ultrasonic transducer rests on said guide surface to transmit ultrasonic waves to said calibration surface.

19. The calibration block of claim 18, wherein said third calibration surface is arcuate and defines a third radius.

20. A method of preparing an ultrasonic transducer to analyze material characteristics, comprising:
emitting an ultrasonic beam incident to a reference block;
rotating said ultrasonic transducer on said reference block to achieve a desired amplitude reflection;
measuring an actual skew angle of said ultrasonic transducer on said reference block.

21. The method of claim 20, further comprising:
calibrating said ultrasonic transducer based on said measured actual skew angle.

22. The method of claim 20, further comprising:
moving said ultrasonic transducer along said reference block to achieve said desired amplitude reflection; and
measuring an actual induced angle of said ultrasonic beam through said reference block.

23. The method of claim 22, further comprising:
calibrating said ultrasonic transducer based on said measured actual induced angle.

24. The method of claim 20, wherein said step of measuring said skew angle comprises:
aligning an angle gauge with a position of said ultrasonic transducer on said reference block; and
reading an angle indicator from said angle gauge to determine said actual skew angle.

* * * * *